United States Patent
Moore, Jr. et al.

(10) Patent No.: US 7,297,842 B2
(45) Date of Patent: Nov. 20, 2007

(54) SOYBEAN

(75) Inventors: Robert E. Moore, Jr., Gibson City, IL (US); Marcos Quiroga Guiraldes, Buenos Aires (AR)

(73) Assignee: Dairyland Seed Co., Inc., West Bend, WI (US)

( * ) Notice: Subject to any disclaimer, the term of this patent is extended or adjusted under 35 U.S.C. 154(b) by 0 days.

(21) Appl. No.: 11/233,523

(22) Filed: Sep. 22, 2005

(65) Prior Publication Data

US 2007/0067878 A1    Mar. 22, 2007

(51) Int. Cl.
*A01H 5/00* (2006.01)
*A01H 5/10* (2006.01)
*A01H 1/00* (2006.01)
*C12N 5/04* (2006.01)

(52) U.S. Cl. .................. 800/312; 800/260; 435/415; 435/421; 435/426; 435/430; 435/430.1

(58) Field of Classification Search ............... 800/260, 800/312; 435/430, 430.1, 415, 426
See application file for complete search history.

(56) References Cited

U.S. PATENT DOCUMENTS 5,523,520 A * 6/1996 Hunsperger et al. ........ 800/260
6,143,954 A    11/2000 Hicks, Jr.
6,570,072 B2 * 5/2003 Eby et al. .................. 800/312

OTHER PUBLICATIONS

Kraft et al (2000, Theor. Appl. Genet. 101:323-326).*
Eshed et al (1996, Genetics 143:1807-1817).*
Hartman, G.L. et al., "Compendium of Soybean Diseases" Fourth Edition, APS Press, St. Paul, MN (1975) 33-35.
Schmitt et al., "Differentiating Soybean Responses to Heterodera Glycines Races," Crop Sci. (1992) 32:275-277.
Schmitthenner, A.F., "*Phytophthora sojae* races in Ohio over a 10-year interval," Plant Disease (1994) 78:269-276.

* cited by examiner

*Primary Examiner*—Stuart F. Baum
(74) *Attorney, Agent, or Firm*—Michael Best & Friedrich LLP

(57) ABSTRACT

Disclosed is the seed of a novel soybean cultivar, designated 5.5 i, a sample of which is deposited under ATCC Accession No. PTA-7273. Also disclosed are plants, or parts thereof, grown from the seed of the cultivar, plants having the morphological and physiological characteristics of the 5.5 i cultivar, and methods of using the plants or parts thereof in a soybean breeding program.

12 Claims, No Drawings

SOYBEAN

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Soybeans are a major grain crop valued for the high levels of oil and protein found in soybean seed. Soybean breeding has resulted in significant improvements in yield potential, stability of yield, adaptation of the species to mechanical harvest, and yield protection through improved disease resistance.

Due to the nature of plant science agriculture, broadly defined as a manipulation of available plant resources to meet the needs of the growing human population, the environment in which plants are grown for agricultural production continuously offers new obstacles to agricultural production. Each new cultivar or variety released to agricultural production is selected for the purpose of increasing yield resulting from increased disease resistance to prevalent diseases, or from direct or indirect improvement in yield potential or efficiency of production. Development of stable, high yielding cultivars with superior characteristics is an ongoing goal of soybean breeders.

There is a need in the art for a novel, superior soybean cultivar and soybean seed.

SUMMARY OF THE INVENTION

In one aspect, the present invention provides a soybean seed designated 5.5 i, wherein a sample of said seed has been deposited under ATCC Accession No. PTA-7273.

In another aspect, the present invention provides a soybean plant, or a part thereof, produced by growing seed designated 5.5 i, or a soybean plant having the characteristics of a plant produced by growing seed designated 5.5 i, or pollen or an ovule of a soybean plant according to the present invention.

The present invention provides a tissue culture of regenerable cells from a plant, or parts thereof, produced by growing seed designated 5.5 i, and a soybean plant regenerated from the tissue culture.

The present invention also provides a method for developing a soybean plant in a soybean breeding program using plant breeding techniques, comprising using a soybean plant, or part thereof, produced by growing seed designated 5.5 i as a source of breeding material.

DEFINITIONS

In the claims, descriptions and tables that follow, numerous terms are used and are defined as follows:

Flower color. Modern soybeans are characterized by two major flower colors, purple or white. Some cultivars are heterogeneous for flower color whereby some plants have purple flowers and some have white.

Leaflet shape. The leaflet may be broad or narrow and may be ovate or oval in shape.

Plant habit refers to stem termination in soybeans and the resultant differences in flower production. Indeterminate varieties continue to grow during the reproductive phase, producing new branches and nodes after flowering is well underway. Determinate varieties tend to delay the onset of flowering somewhat, and limit new node and branch development after flowering has been initiated.

Pubescence relates to the plant trichomes or hairs found on the stems, leaves and pods of soybeans.

Pubescence color in modern soybeans may be tawny, gray or light tawny.

Pod color refers to the color of the mature pod wall, as distinct from the color of the pubescence, and in modern soybeans, may be brown or tan.

Hilum refers to the point of attachment of soybean seed to maternal tissue.

Hilum color in modern soybeans may be black, brown, yellow, gray, buff, or imperfect black.

Plant height is measured from the top of soil to top node of the plant in any convenient unit of length (i.e., inches, centimeters). For the data presented herein, plant height was measured just prior to harvest and is expressed in inches.

Lodging resistance relates to the stature of the plant relative to the ground. Lodging resistance is rated on a scale of 1 to 5. A score of 1 is given to an erect plant. A score of 2.5 is given to a plant that is leaning at a 45-degree angle relative to the ground. A score of 5 indicates a plant lying on the ground.

Maturity date is the date when 95% of pods have turned color from green color to their mature brown or tan color. The maturity date is counted in days and is calculated from planting date until 95% maturity.

Maturity group refers to an industry division of groups of varieties based on the zones in which the varieties are adapted. Soybeans mature differentially in response to day-length and thus to latitude where grown. In the soybean production areas of the United States, for example, the northernmost production region of northern Minnesota is planted to soybeans that mature under very long day-lengths during early summer. In the southernmost production regions of the Southeast, soybeans that mature from the influence of short day-length during early summer are grown. Those adapted to northern day-lengths are classified as early-maturing, those adapted to the southern regions are classified as late-maturing. Maturity groups include very long day length varieties (000, 00, 0) and extend to very short day length varieties (VII, VII, IX, X). For example, maturity group I soybean cultivars are typically grown in southern Minnesota, whereas maturity group V soybean cultivars are typically group in the mid-south.

Relative maturity. Within maturity groups, a more precise maturity assignment is given that subdivides each maturity group into tenths. For example, a relative maturity of 3.3 is assigned to a late early maturity group III soybean cultivar.

Yield refers to the yield of seed harvested from a soybean crop. Yield data presented herein is expressed as bushels of seed/acre and is the actual yield of the grain at harvest.

Soybean Cyst Nematode (SCN) resistance is based on a comparison of reproduction rates to a known susceptible cultivar as described by Schmitt et al. (Crop Sci. 32:275-277, 1992), which is incorporated by reference herein. A cultivar with a 0-10% percent reproductive rate compared to a known susceptible cultivar is classified as resistant (R); a cultivar with an 11-30% reproductive rate compared to a known susceptible cultivar is classified as moderately resistant (MR); a cultivar with an 31-59% reproductive rate compared to a known susceptible cultivar is classified as moderately susceptible (MS).

Southern Stem Canker resistance refers to the casual organism *Diaporthe phaseolorum meridionalis*. There are 4 genes for resistance as described by G. L. Hartman, J. B. Sinclair and J. C. Rupe (Compendium of Soybean Diseases—Fourth Edition). In the field, disease development is associated with early infection and the level of cultivar resistance.

Phylophthora Root Rot resistance refers to the casual organism, *P. sojae*. A. F. Schmitthenner (Plant Disease 78:269-276). Certain cultivars can have race-specific resistance. Resistance results in an incompatible interaction in which the fungus fails to colonize tissue beyond a hypersensitive fleck-type lesion. (G. L. Hartman, J. B. Sinclair and J. C. Rupe, Compendium of Soybean Diseases—Fourth Edition).

DETAILED DESCRIPTION OF THE INVENTION

Soybean cultivar 5.5 i has superior characteristics and was developed from crossing two elite soybean varieties. Criteria used to select in various generations included seed yield, lodging resistance, emergence, disease resistance and tolerance, maturity, late season plant intactness, plant height, and shattering resistance. $F_1$ and $F_2$ plants were advanced by a modified single seed descent selection. $F_2$-derived $F_3$ plants were grown, tested and bulk-harvested. In Argentina, $F_4$ plants were selected from the original F3 bulk and further tested for yield and purity. From these $F_4$ selections, the line now known as 5.5 i, was selected. In addition, it was tested for yield, agronomics and disease reactions in over 14 locations in a two year span in Argentina. Production of 5.5 i was performed in both Argentina and the US.

Soybean cultivar 5.5 i is a late group V variety, with a relative maturity of 5.5. The cultivar has very high yield potential, relative to lines of similar maturity, and excellent agronomic characteristics, including lodging resistance. Soybean cultivar 5.5 i is resistant to the Roundup™ herbicides.

Soybean cultivar 5.5 i has uniformity and stability of its morphological and other characteristics. The variety description information (Table I) provides a summary of characteristics of soybean cultivar 5.5 i plant characteristics. As used herein, "a soybean plant having the physiological and morphological characteristics of soybean cultivar 5.5 i is a plant having the characteristics set forth in Table 1.

TABLE 1

VARIETY DESCRIPTION INFORMATION

Seed coat color: Yellow
Hilum color: Yellow
Leaflet size: Medium
Leaflet color: Medium to Dark Green
Leaflet shape: Ovate
Flower Color: White
Plant habit: Indeterminate
Pubescence color: Gray
Pod color: Brown
Maturity group: V
Relative maturity: 5.5
Phytophthora Root Rot resistance: Rps1a
Soybean Cyst Nematode Disease: Susceptible TABLE 1-continued

VARIETY DESCRIPTION INFORMATION

Southern Stem Canker: Resistant
Roundup ™ Herbicide: Resistant to Roundup Ready ™

Table 2 shows plant height and lodging scores for cultivar 5.5 i compared to that of other known commercial cultivars.

TABLE 2

Summary of plant height and lodging scores of soybean cultivar 5.5 i, compared to several competing varieties of commercial soybeans of similar maturity.

| Years | Cultivar | Height | Lodging |
|---|---|---|---|
| 2 | 5.5 i | 45 | 2.8 |
|   | A5409 | 43 | 3.1 |
| 2 | 5.5 i | 45 | 2.8 |
|   | A5417 | 33 | 3.8 |
| 1 | 5.5 i | 45 | 2.0 |
|   | A5520 | 33 | 2.0 |
| 1 | 5.5 i | 45 | 2.0 |
|   | A5901 | 41 | 1.7 |
| 1 | 5.5 i | 45 | 2.0 |
|   | MARIA55 | 43 | 4.0 |

TABLE 3

Summary of yield and maturity data of soybean cultivar 5.5 i versus other commercial soybean cultivars.

| Years | Cultivar | Reps | Yield | Mat Days |
|---|---|---|---|---|
| 2 | 5.5 i | 29 | 76.0 | +4 |
|   | A5409 |   | 63.3 | 0 |
| 2 | 5.5 i | 29 | 76.0 | +2 |
|   | A5417 |   | 68.3 | 0 |
| 1 | 5.5 i | 21 | 72.7 | 0 |
|   | A5520 |   | 64.2 | 0 |
| 1 | 5.5 i | 21 | 72.7 | −5 |
|   | A5901 |   | 64.1 | 0 |
| 2 | 5.5 i | 29 | 76.0 | −4 |
|   | A6411 |   | 71.3 | 0 |
| 2 | 5.5 i | 27 | 74.1 | −4 |
|   | DM5800 |   | 66.3 | 0 |
| 1 | 5.5 i | 21 | 72.7 | +4 |
|   | MARIA55 |   | 59.0 | 0 |
| 1 | 5.5 i | 21 | 72.7 | −3 |
|   | RAR514 |   | 68.8 | 0 |

The present invention contemplates using the 5.5 i soybean plant, or part thereof, or a soybean plant having the physiological and morphological characteristics of the 5.5 i soybean plant, as a source of breeding material for developing a soybean plant in a soybean breeding program using plant breeding techniques. Plant breeding techniques useful in the developing soybean plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature. For example, see U.S. Pat. No. 6,143,954, which, along with the references cited therein, is incorporated by reference herein.

As used herein, the term "plant" includes plant cells, plant protoplasts, plant cell tissue cultures from which soybean plants can be regenerated, plant calli, plant clumps, and plant cells that are intact in plants or parts thereof. "Plant part" includes, but is not limited to, embryos, pollen, ovules, seeds, flowers, pods, leaves, roots, root tips, anthers, and the like.

One may obtain soybean plants according to the present invention by directly by growing the seed of 5.5 i or by any other means. A soybean plant having all of the physiological and morphological characteristics of 5.5 i can be obtained by any suitable means, including, but not limited to, regenerating plants or plant parts from tissue culture or cuttings. The scope of the present invention is not limited by the method by which the plant is obtained.

DEPOSIT INFORMATION

Seed from soybean cultivar 5.5 i, disclosed above and recited in the appended claims, was deposited with the American Type Culture Collection (ATCC), 10801 University Boulevard, Manassas, Va. 20110 on Dec. 15, 2005.

The present invention is not limited to the exemplified embodiments, but is intended to encompass all such modifications and variations as come within the scope of the following claims.

We claim:

1. A soybean seed designated 5.5 i, wherein a sample of said seed has been deposited under ATCC Accession No. PTA-7273.

2. A plant, or a part thereof, produced by growing the seed of claim 1.

3. Pollen of the plant of claim 2.

4. An ovule of the plant of claim 2.

5. A soybean plant, or a part thereof, having all the physiological and morphological characteristics of the soybean plant of claim 2.

6. A tissue culture of regenerable cells from the plant, or part thereof, of claim 2.

7. A soybean plant regenerated from the tissue culture of claim 6, wherein the plant has all of the physiological and morphological characteristics of a plant produced by growing seed designated 5.5 i and deposited under ATCC Accession No. PTA-7273.

8. The tissue culture of claim 6, wherein the regenerable cells selected from the group consisting of protoplasts and calli and wherein the regenerable cells are derived from a plant part selected from the group consisting of leaf, pollen, ovule, cotyledon, hypocotyl, embryo, root, pod, flower, shoot and stalk.

9. A method for developing a soybean plant in a soybean breeding program using plant breeding techniques, comprising using the soybean plant, or part thereof, of claim 2 as a source of breeding material.

10. The method of claim 9 wherein said plant breeding techniques are selected from the group consisting of single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation.

11. A method for producing an $F_1$ progeny of soybean cultivar 5.5 i, comprising:
    (a) crossing soybean cultivar 5.5 i with a second soybean plant to yield an $F_1$ progeny soybean seed; and
    (b) growing said $F_1$ progeny seed to yield a soybean cultivar 5.5 i derived soybean plant.

12. An $F_1$ progeny of soybean cultivar 5.5 i, or parts thereof, produced by the method of claim 11.

* * * * *